United States Patent
Fogarty et al.

(10) Patent No.: US 7,900,346 B2
(45) Date of Patent: Mar. 8, 2011

(54) INSPECTION SENSOR MOUNTS AND A METHOD FOR MOUNTING AN INSPECTION SENSOR

(75) Inventors: Michael D. Fogarty, Auburn, WA (US); Gary E. Georgeson, Federal Way, WA (US); Daniel J. Wright, Mercer Island, WA (US); Lyle R. Deobald, Shoreline, WA (US)

(73) Assignee: The Boeing Company, Chicago, IL (US)

( * ) Notice: Subject to any disclaimer, the term of this patent is extended or adjusted under 35 U.S.C. 154(b) by 765 days.

(21) Appl. No.: 11/818,871

(22) Filed: Jun. 15, 2007

(65) Prior Publication Data
US 2008/0307637 A1    Dec. 18, 2008

(51) Int. Cl.
*B23P 19/00* (2006.01)
(52) U.S. Cl. .................. 29/761; 29/595; 29/832; 73/644; 248/73
(58) Field of Classification Search .............. 73/618, 73/622, 624, 629, 634, 644, 861.18, 966.5; 181/124; 248/73, 74.1; 294/64.1; 293/117; 29/595, 705, 721, 729, 743, 760, 830–832
See application file for complete search history.

(56) References Cited

U.S. PATENT DOCUMENTS

| | | | | |
|---|---|---|---|---|
| 3,942,358 | A * | 3/1976 | Pies | 73/624 |
| 4,019,373 | A * | 4/1977 | Freeman et al. | 73/644 |
| 6,945,111 | B2 | 9/2005 | Georgeson | |
| 6,945,113 | B2 * | 9/2005 | Siverling et al. | 73/622 |
| 7,240,556 | B2 | 7/2007 | Georgeson et al. | |
| 7,249,512 | B2 | 7/2007 | Kennedy et al. | |
| 7,313,959 | B2 | 1/2008 | Georgeson et al. | |
| 7,357,431 | B2 * | 4/2008 | Sato et al. | 293/117 |
| 7,367,236 | B2 | 5/2008 | Georgeson et al. | |
| 7,484,413 | B2 | 2/2009 | Georgeson et al. | |
| 7,614,304 | B2 | 11/2009 | Gunasekaran et al. | |
| 7,706,985 | B2 | 4/2010 | Fogarty et al. | |

* cited by examiner

*Primary Examiner* — Donghai D. Nguyen
(74) *Attorney, Agent, or Firm* — Toler Law Group

(57) ABSTRACT

In non-limiting, exemplary embodiments a mount assembly is provided for mounting an inspection sensor to a surface of a workpiece. The mount assembly includes a mount having an attachment portion and an engagement portion. The attachment portion is arranged to attach the mount to the surface of the workpiece. The engagement portion is arranged to engage the inspection sensor with the mount. Exemplary mount assemblies may be arranged to mount pulse echo ultrasonic testing transducers, focused ultrasonic testing transducers, through transmission ultrasonic testing transducers, eddy current inspection sensors, or any type of inspection sensor as desired.

6 Claims, 6 Drawing Sheets

INSPECTION SENSOR MOUNTS AND A METHOD FOR MOUNTING AN INSPECTION SENSOR

BACKGROUND

Ultrasonic testing (UT) is frequently used to perform non-destructive inspection (NDI) of a unit under test (UUT). UT is especially well-suited for inspecting for discontinuities in a material, such as delaminations or disbanding in composite materials. To perform such inspections, currently an operator must hold a UT transducer in place against a surface of a UUT.

The operator can monitor one location at a time, and may not be able to locate a UT transducer with desired accuracy or repeatability. An operator may not be able to obtain or maintain desired ultrasonic coupling of a UT transducer with the UUT. Further, for personnel safety purposes an operator must wait until a UUT is no longer under load to perform UT inspection, thereby precluding real-time UT of a UUT that is under load. Thus, improvements in UT may be possible regarding time reductions, accuracy, repeatability, and obtaining real-time data of a UUT under load.

The foregoing examples of related art and limitations associated therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems and methods which are meant to be exemplary and illustrative, not limiting in scope. In various embodiments, one or more of the problems described above in the Background have been reduced or eliminated, while other embodiments are directed to other improvements.

In non-limiting, exemplary embodiments, a mount assembly is provided for mounting an inspection sensor to a surface of a workpiece. The mount assembly includes a mount having an attachment portion and an engagement portion. The attachment portion is arranged to attach the mount to the surface of the workpiece. The engagement portion is arranged to engage the inspection sensor with the mount.

According to an aspect, mount assemblies may be arranged to mount pulse echo ultrasonic testing transducers, focused ultrasonic testing transducers, through transmission ultrasonic testing transducers, eddy current inspection sensors, or any type of inspection sensor.

In addition to the exemplary embodiments and aspects described above, further embodiments and aspects will become, apparent by reference to the drawings and by study of the following detailed description.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

By way of overview, in non-limiting, exemplary embodiments a mount assembly is provided for mounting an inspection sensor to a surface of a workpiece. The mount assembly includes a mount having an attachment portion and an engagement portion. The attachment portion is arranged to attach the mount to the surface of the workpiece. The engagement portion is arranged to engage the inspection sensor with the mount. Exemplary mount assemblies may be arranged to mount pulse echo ultrasonic testing transducers, focused ultrasonic testing transducers, and through transmission ultrasonic testing transducers. While exemplary mounts disclosed herein are illustrated in the context of ultrasonic inspection methods, exemplary embodiments are not intended to be limited to use with ultrasonic testing transducers. Exemplary mounts disclosed herein may also be used with any type of inspection sensor as desired, such as without limitation sensors for eddy current inspection or any other inspection method as desired for a particular application, and no limitation whatsoever is intended. Details of exemplary, non-limiting embodiments will now be set forth below.

Figure 1A:
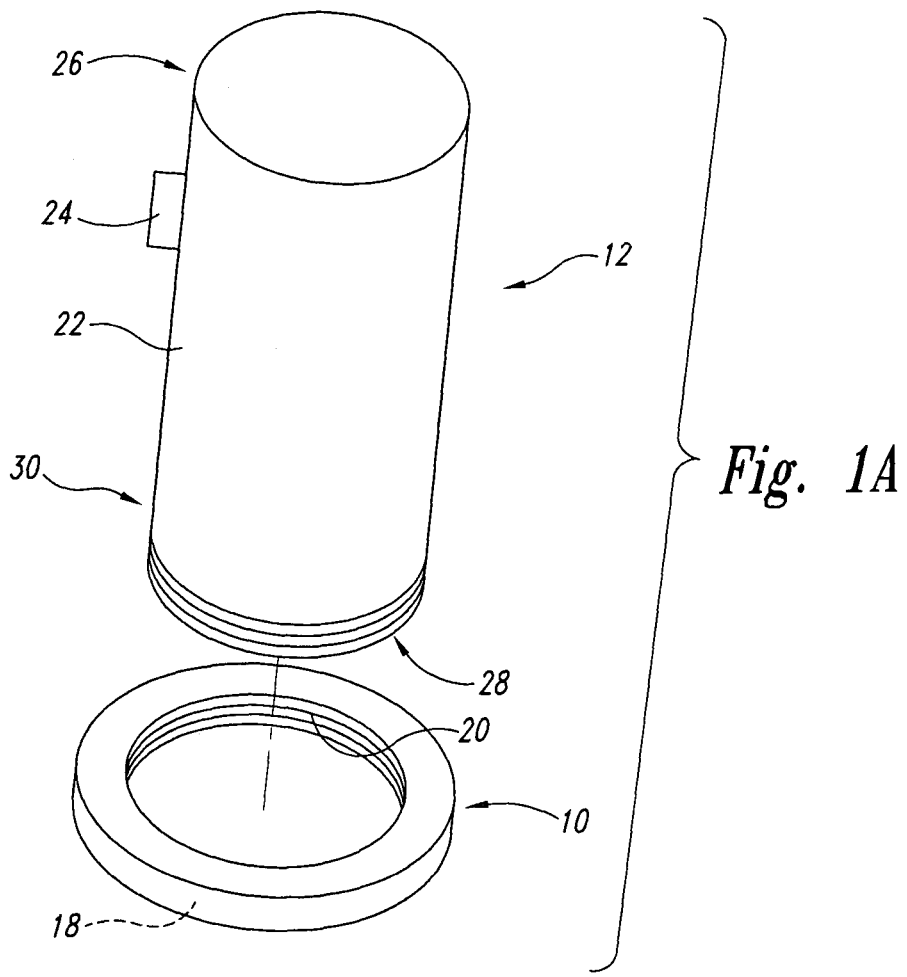
FIG. 1A is a perspective view of an exemplary pulse echo ultrasonic testing transducer and an exemplary ring surface mount.
Figure 1B:
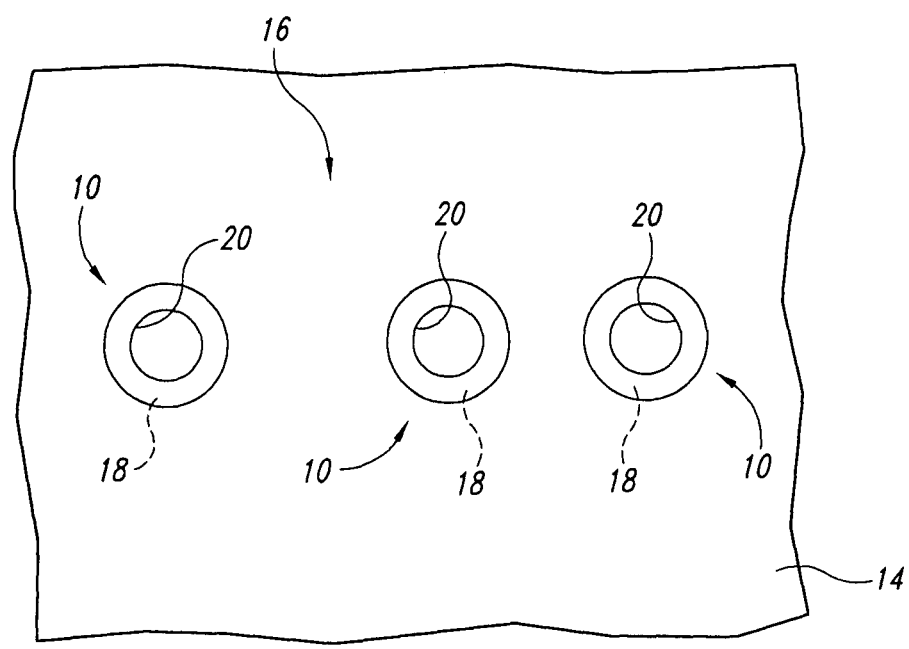
FIG. 1B is a top plan view of the exemplary ring surface mounts of FIG. 1A.

Referring now to FIGS. 1A and 1B, a mount assembly 10 can mount a pulse echo ultrasonic testing (UT) transducer 12 to a surface of a workpiece or unit under test (UUT). The mount assembly 10 may be capable of handling large strains and may be suitable for many applications as desired.

In this non-limiting embodiment, the mount assembly is a surface ring. The surface ring 10 has a substantially planar surface 18 arranged to attach the surface ring 10 to the surface 14. For example, the surface 18 may be adhered to the surface 14 with a suitable adhesive as desired for a particular application. The surface ring 10 has a threaded inner surface 20.

The pulse echo UT transducer 12 suitably has a cylindrical body 22. An electrical connection port 24 is provided toward an upper portion 26 of the cylindrical body 22. Threads 28 are defined around the exterior of a lower portion 30 of the body 22.

The body 22 is rotated in the surface ring 10 so the threads 20 threadedly engage the threads 28. When the body 22 is completely threaded into the surface ring 10, the pulse echo UT transducer 12 is securely mounted to the UUT 16.

Figure 2A:
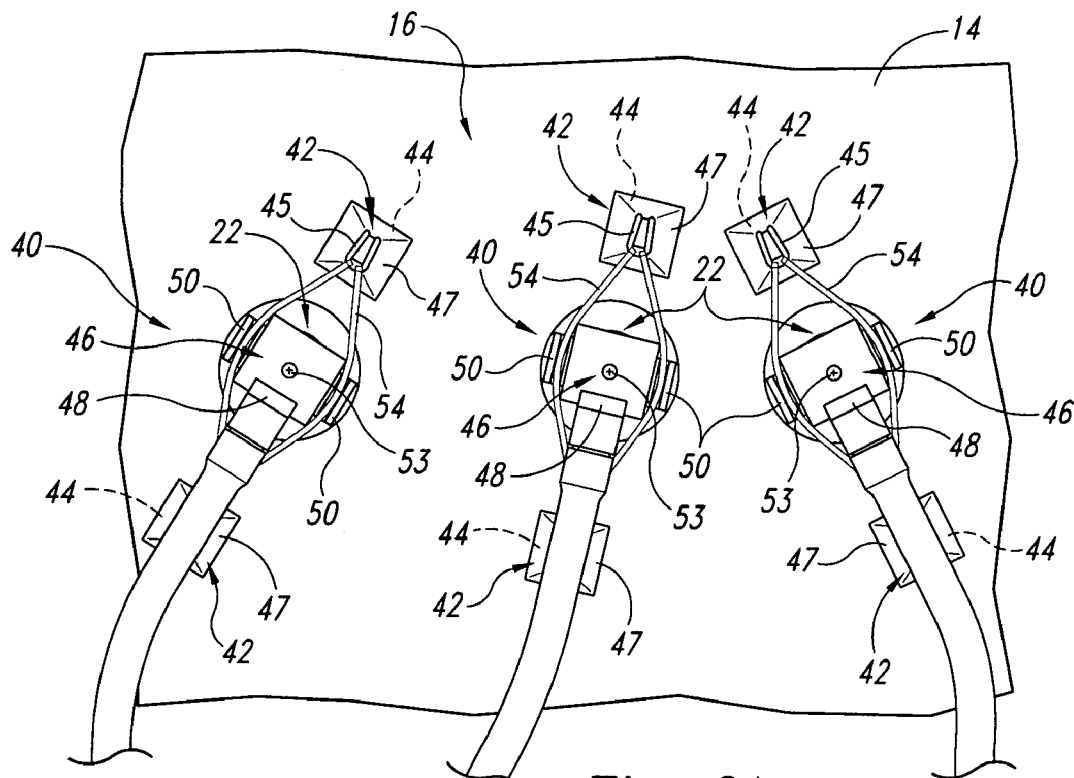
FIG. 2A is a top plan view of pulse echo ultrasonic testing transducers mounted with an exemplary externally-biased cap.
Figure 2B:
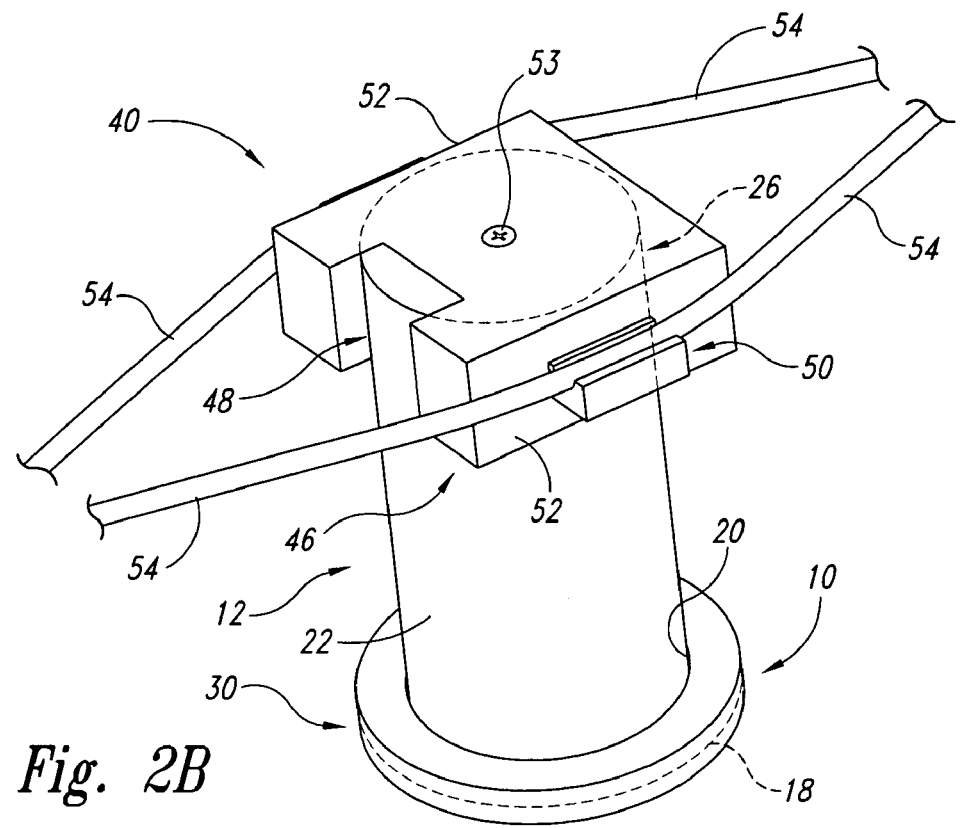
FIG. 2B is a perspective view of the pulse echo ultrasonic testing transducer of FIG. 1A mounted with the ring surface mount of FIG. 1A and the externally-biased cap of FIG. 2A.

Referring now to FIGS. 2A and 2B, a mount assembly 40 can mount a pulse echo UT transducer to the surface 14 of the UUT 16. In one embodiment, the pulse echo UT transducer can be threaded such as the pulse echo UT transducer 12. In another embodiment, the pulse echo UT transducer need not be threaded. As with the mount assembly 10 (FIGS. 1A and 1B), the mount assembly 40 may be capable of handling large strains.

Attachment pads 42 each have a surface 44 arranged to adhere to the surface 14. For example, the surface 44 may be adhered to the surface 14 with a suitable adhesive as desired for a particular application. Each attachment pad 42 has an attachment loop 45 that extends from an upper surface 47 of the attachment pad 42.

A hold-down cap 46 is arranged to receive therein the upper portion 26 of a pulse echo UT transducer, such as the pulse echo UT transducer 12 (or a pulse echo UT transducer without threads). A cut-out 48 defined in the hold-down cap 46 accommodates the electrical connection port 24, thereby permitting the hold-down cap 46 to be placed upon the upper portion 26. Flanges 50 extend from opposite sides 52 of the hold-down cap 46. A de-biasing screw 53 is provided through a hole (not shown) in the center of the top of the hold-down cap 46. The de-biasing screw 53 allows the transducer to be driven against the surface 14 by a point source.

A biasing member 54 is looped through the attachment loops 45 and is placed onto the flanges 50, thereby biasing the hold-down cap 46 against the upper portion 26 of a pulse echo UT transducer. The biasing member 54 may be an elastomeric band.

In one embodiment (and as illustrated in FIG. 2A) the portion 30 of the pulse echo UT transducer need not be threaded. In such a case, the surface ring 10 need not be used with the mounting assembly 40. The mount assembly 40 can thus handle large strains as a standalone mount assembly and may be suitable for many applications as desired.

In another embodiment (and as illustrated in FIG. 2B), the portion 30 of the pulse echo UT transducer is threaded and the surface ring 10 can be used with the mounting assembly 40. Use of the surface ring 10 along with the mounting assembly 40 can thus provide for redundant attachment to the UUT 16 and can accommodate even larger strains than can either the surface ring 10 or the mount assembly 40 alone.

Figure 3:
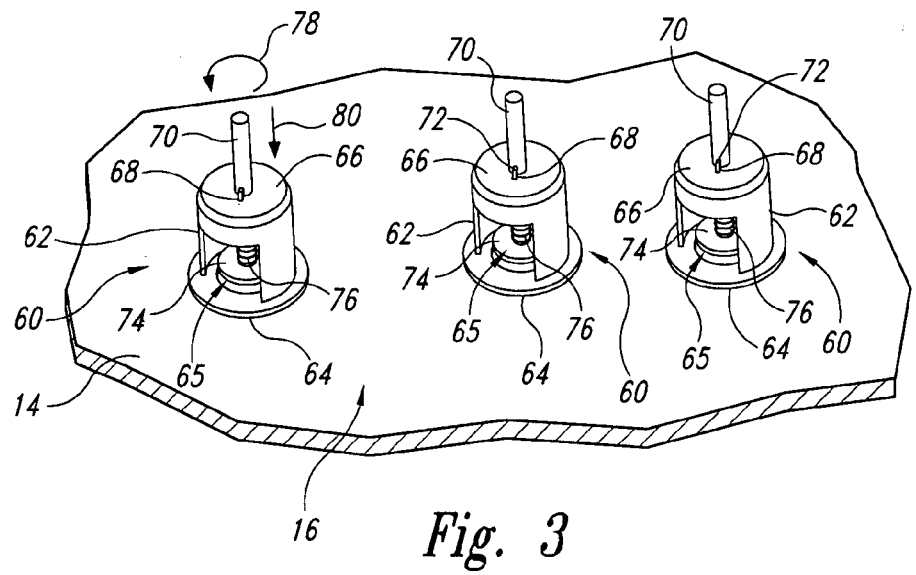
FIG. 3 is a perspective view of self-biasing canister mounts for pulse echo ultrasonic testing transducers.
Figure 4A:
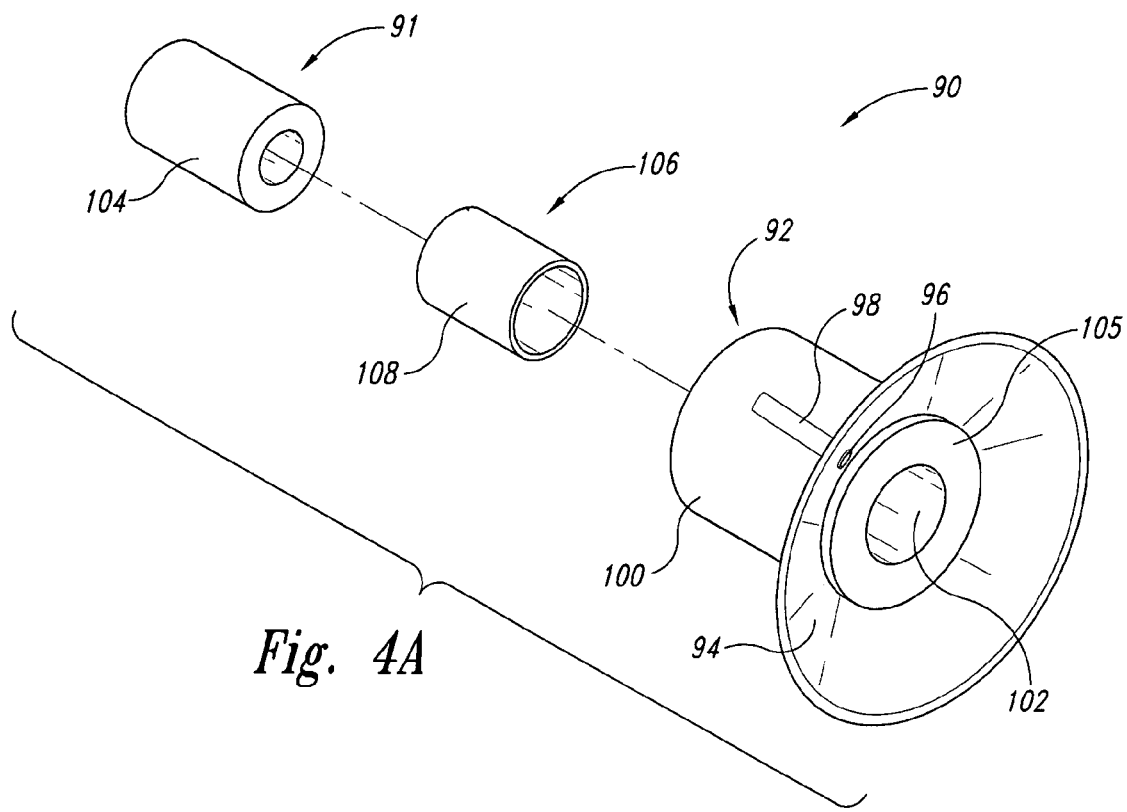
FIG. 4A is an exploded perspective view of an exemplary vacuum mount and a focused beam pulse echo ultrasonic testing transducer.
Figure 4B:
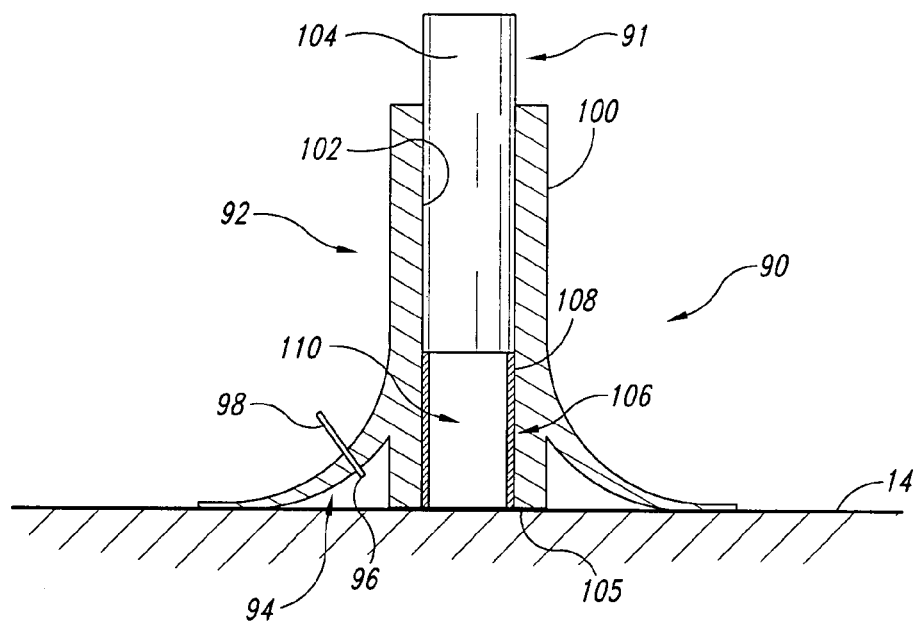
FIG. 4B is a cutaway side plan view of the vacuum mount and focused beam pulse echo ultrasonic testing transducer of FIG. 4A.
Figure 4C:
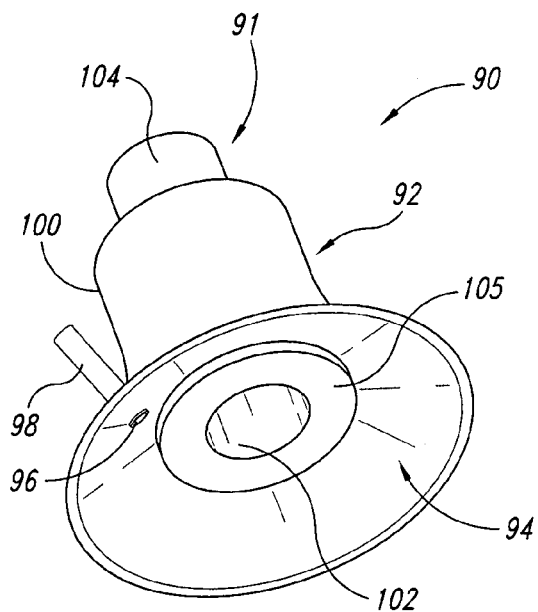
FIGS. 4C and 4D are perspective views of the vacuum mount and focused beam pulse echo ultrasonic testing transducer of FIG. 4A.
Figure 4D:
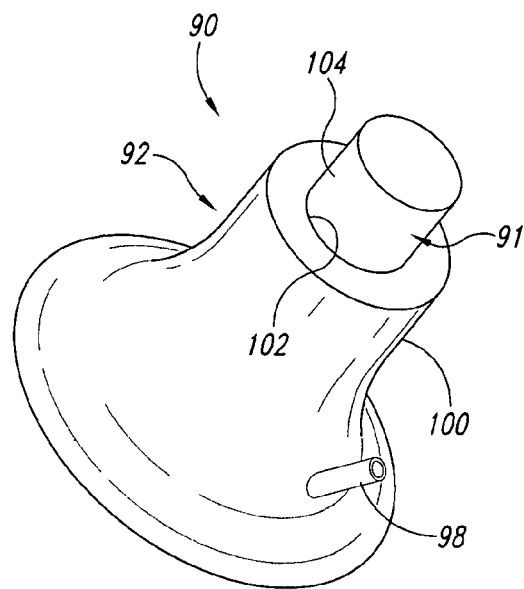

Referring now to FIG. 3, a mount assembly 60 can mount a pulse echo UT transducer to the surface 14 of the UUT 16. The mount assembly 60 can be used where space is limited or where interference is present.

A canister 62 is arranged to receive therein a pulse echo UT transducer (not shown). The canister 62 has a substantially planar surface 64 arranged to attach the canister 62 to the surface 14. For example, the surface 64 may be adhered to the surface 14 with a suitable adhesive as desired for a particular application. An opening 65 is defined in the canister 62.

A surface 66 of the canister 62 defines a central hole with a slit 68 extending radially outward therefrom. A push rod 70 is received in the central hole. A tab 72 extends radially outward from the push rod 70. Inside the canister 62 a plunger 74 is attached to an end of the push rod 70. A biasing device 76 is interposed between the plunger 74 and the surface 66 of the canister 62. For example, the biasing device 76 may be a spring that is coiled around the push rod 70 inside the canister 62.

A pulse echo UT transducer (not shown) is placed in the canister 62 through the opening 65. The push rod 70 is rotated as shown by an arrow 78 until the tab 72 aligns with the slit 68. The biasing device 76 urges the plunger 74 and the push rod 70 in a direction as shown by an arrow 80. The plunger 76 thus engages an upper portion of the pulse echo UT transducer and urges the pulse echo UT transducer against the surface 14 of the UUT 16.

Referring now to FIGS. 4A-4D, a mount assembly 90 can mount a focused pulse echo UT transducer 91 to the surface 14 of the UUT 16. The mount assembly 90 is held to the surface 14 of the UUT 16 using a vacuum (either temporary or continuous). The mount assembly 90 is flexible, thereby allowing part deformation without affecting test results and minimizing separation issues under high strains. The mount assembly 90 also does not entail being adhesively bonded to a surface of a part.

A vacuum cup 92 has a suction ring 94. The vacuum cup 92 is suitably made of rubber. Thus, the mount assembly 90 is flexible. The suction ring 94 defines a vacuum port 96. A vacuum line 98 may be connected to the vacuum port 96 to draw a continuous vacuum within the suction ring 94 for mounting the vacuum cup 92 to the surface 14 and maintaining the mount assembly 90 continuously attached to the surface 14 via the continuous vacuum. For example, use of a continuous vacuum can help ensure that the mount assembly 90 remains attached to the surface 14 throughout a mechanical test of the UUT 16. However, if desired the mount assembly 90 may be attached to the surface 14 via a temporary vacuum. For example, the self-vacuum of the suction ring 94 on the surface 14 can attach the mount assembly to the surface 14 for several hours.

A core 100 of the vacuum cup 92 extends from the suction ring 94. The core 100 has an inner cylindrical surface 102. The inner cylindrical surface 102 is sized to engage an outer cylindrical surface 104 of the focused pulse echo UT transducer 91, thereby maintaining the focused pulse echo UT transducer 91 within the mount assembly 90 via interference fit. A seal 105 is disposed at an end of the core 100 toward the suction ring 94. The seal 105 sealingly engages the surface 14 and seals the core 100 from the surface 14 as vacuum holds the vacuum cup 92 to the surface 14.

A stand-off sleeve 106 has a cylindrical outer surface 108. The stand-off sleeve 106 maintains the focused pulse echo UT transducer 91 spaced apart from the surface 14 of the UUT 16. The stand-off sleeve 106 suitably is made of plastic or metal, as desired for a particular application. As such, the stand-off sleeve 106 can give the mount assembly 90 additional stiffness. The stand-off sleeve 106 is received in the core 100 toward the suction ring 94. The inner cylindrical surface 102 is sized to engage an outer cylindrical surface 104 of the focused pulse echo UT transducer 91, thereby maintaining the focused pulse echo UT transducer 91 within the mount assembly 91 via interference fit.

The stand-off sleeve 106 helps ensure that the focal length of the focused pulse echo UT transducer 91 is near the region where failure of the UUT 16 may first appear, thereby helping to increase sensitivity to any possible damage. The core 100 is filled with an ultrasonic couplant 110, such as without limitation water. The edge of the core 100 is sealed at the seal 105 by the vacuum at the surface 14 of the UUT 16, thereby helping to minimize any solid interfaces along the ultrasonic signal path that might contribute to reflections and signal losses. This is because there is only the ultrasonic couplant 110 between the transducer and the part surface. The focused pulse echo UT transducer 91 is slid into the core 100, which has enough interference to provide a snug fit. It will be appreciated that any air bubbles in the core 100 between the focused pulse echo UT transducer 91 and the surface 14 should be removed. If desired, an optional, separate ultrasonic couplant inlet (not shown) and ultrasonic couplant outlet (not shown) may be provided if a particular mounting orientation (such as upside down) makes insertion of the ultrasonic couplant 110 and removal of any bubbles difficult.

Figure 5A:
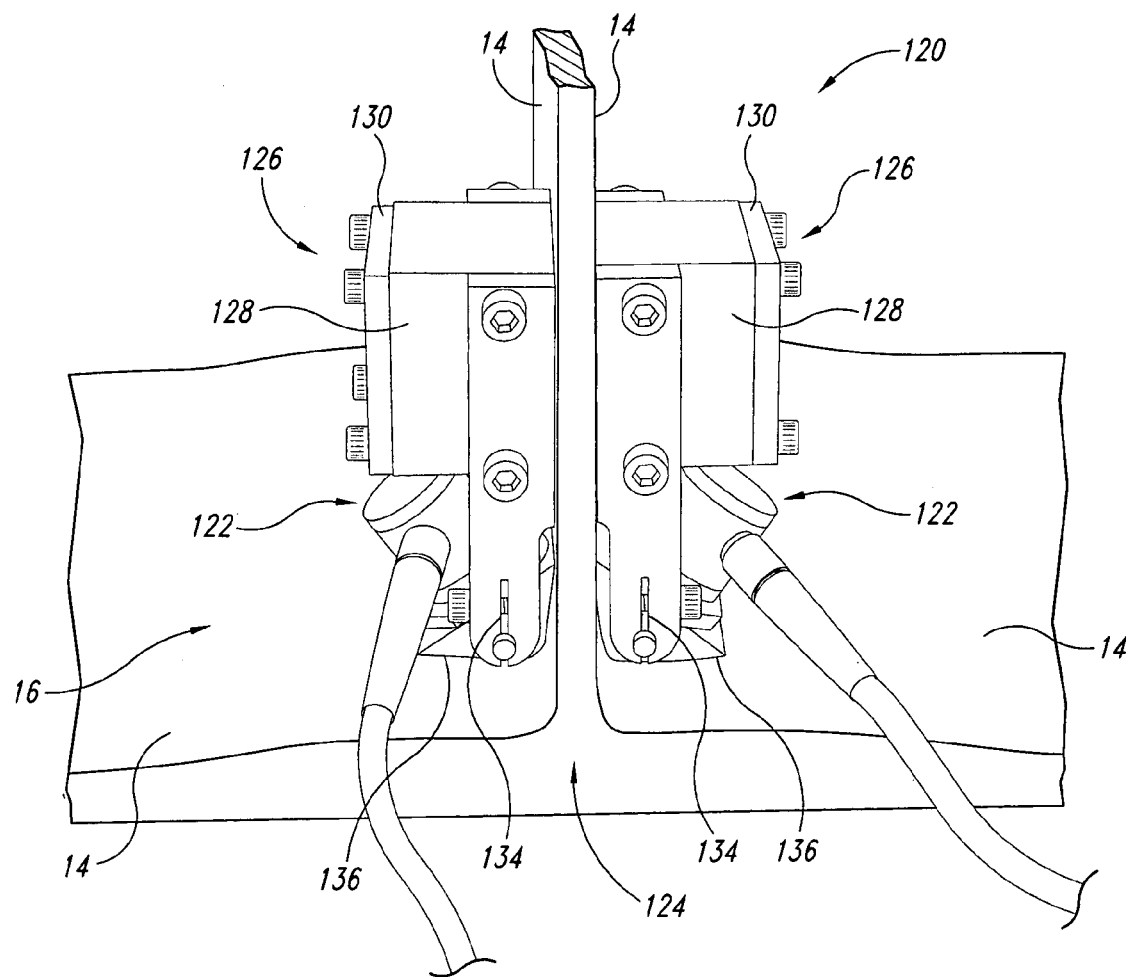
FIG. 5A is a side plan view of exemplary through transmission ultrasonic testing transducers mounted in exemplary magnetic angled mounts.
Figure 5B:
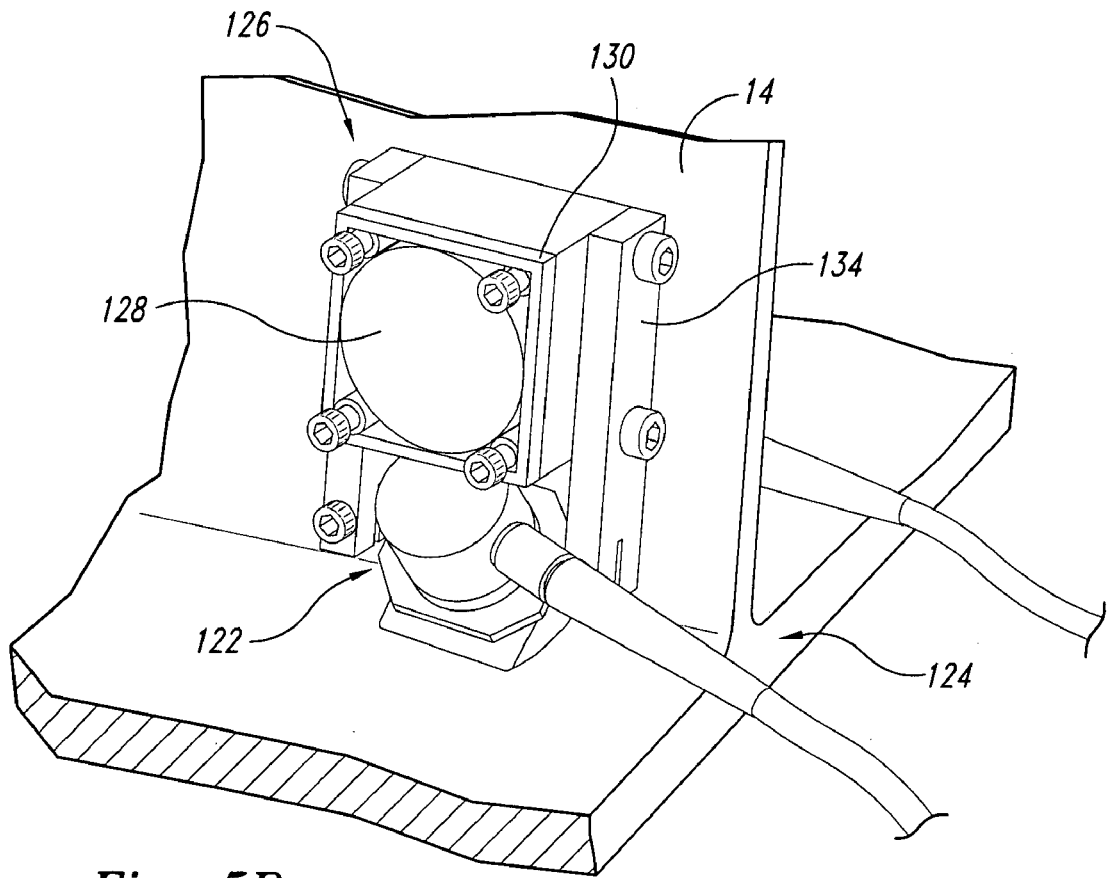
FIG. 5B is a perspective view of one of the magnetically mounted angled through transmission ultrasonic testing transducers of FIG. 5A.
Figure 5C:
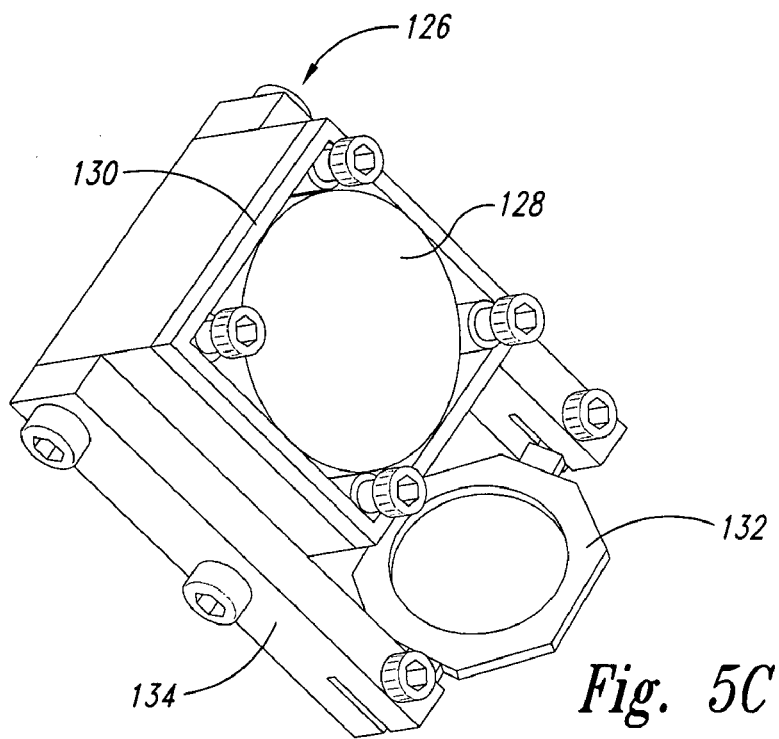
FIG. 5C is a perspective view of one of the exemplary magnetic angled mounts of FIG. 5A.

Referring now to FIGS. 5A-5C, a mount assembly 120 can mount a pair of through transmission UT transducers 122 to surfaces 14 of the UUT 16. The mount assembly 120 magnetically mounts the through transmission UT transducers 122 and is well-suited for enabling non-destructive inspection and monitoring of a joint 124 in the UUT 16.

The mount assembly 120 includes a transducer mount 126 for each of the through transmission UT transducers 122. A magnet 128 is installed in each transducer mount 126, such as by being retained in place by a retaining frame 130. The magnets 128 are oriented relative to each other such that their domains are aligned to magnetically attract each other, thereby magnetically attaching each transducer mount 126 to its respective surface 14 disposed therebetween near the joint 124.

A transducer mounting ring 132 is attached to a mounting frame 134 of each of the transducer mounts 126. The transducer mounting ring 132 receives therein the through transmission UT transducer 122. In exemplary embodiments, the transducer mounting ring 132 is attached to the mounting frame 134 at any angle as desired for a particular application, such as for orienting the through transmission UT transducers to transmit and receive ultrasonic energy to and from the joint 124.

Wave guides 136 ultrasonically couple ultrasonic energy between the through transmission UT transducers 122 and the UUT 16. The wave guides 136 may be made of any material that provides a medium having a suitable coefficient of transmission for the ultrasonic energy. Given by way of non-limiting example, the wave guides 136 may be provided in the form of elastomeric stand-offs.

While a number of exemplary embodiments and aspects have been illustrated and discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A mount assembly for mounting an inspection sensor to a surface of a workpiece, the mount assembly comprising:
   a mount having:
      an attachment portion arranged to attach the mount to a surface of a workpiece by adhering a surface of the attachment portion to the surface of the workpiece, the attachment portion including:
         a first attachment member that includes a substantially planar surface of a ring; and
         a second attachment member that includes a pair of attachment pads arranged to adhere to the surface of the workpiece; and
      an engagement portion arranged to engage an inspection sensor with the mount such that the inspection sensor is removable without removing the attachment portion from the surface of the workpiece, the engagement portion including:
         a first engagement member that includes a threaded inner surface of the ring that is arranged to threadedly engage a threaded portion of an outer surface of the inspection sensor; and
         a second engagement member that includes a cap arranged to receive therein an upper portion of the inspection sensor and a biasing member attached to the pair of attachment pads and arranged to bias the cap against the upper portion of the inspection sensor.

2. A mount assembly for mounting an inspection sensor to a surface of a workpiece, the mount assembly comprising:
   a ring member having:
      a substantially planar surface arranged to attach the ring member to a surface of a workpiece; and
      a threaded inner surface that is arranged to threadedly engage a threaded portion of an outer surface of an inspection sensor;
   a pair of attachment pads having a first surface arranged to adhere to the surface of the workpiece;
   a cap arranged to receive therein an upper portion of the inspection sensor; and
   a biasing member attached to a second surface of the pair of attachment pads and arranged to bias the cap against the upper portion of the inspection sensor.

3. The mount assembly of claim 2, wherein the biasing member includes an elastomeric band.

4. The mount assembly of claim 2, wherein:
   the cap includes first and second flanges extending from first and second sides of the cap; and
   the first and second flanges receive the biasing member thereon.

5. A mount assembly for mounting an inspection sensor to a surface of a workpiece, the mount assembly comprising:
   a mount having:
      an attachment portion arranged to attach the mount to a surface of a workpiece, the attachment portion including:
         a first attachment member that includes a substantially planar surface of a ring; and
         a second attachment member that includes a pair of attachment pads arranged to adhere to the surface of the workpiece; and
      an engagement portion arranged to engage an inspection sensor with the mount, the engagement portion including:
         a first engagement member that includes a threaded inner surface of the ring that is arranged to threadedly engage a threaded portion of an outer surface of the inspection sensor; and
         a second engagement member that includes a cap arranged to receive therein an upper portion of the inspection sensor and a biasing member attached to the pair of attachment pads and arranged to bias the cap against the upper portion of the inspection sensor.

6. A method of mounting an inspection sensor to a surface of a workpiece, the method comprising:
   adhering an attachment portion of a mount to a surface of a workpiece, the attachment portion including:
      a first attachment member that includes a substantially planar surface of a ring; and
      a second attachment member that includes a pair of attachment pads arranged to be adhered to the surface of a workpiece; and
   engaging an inspection sensor with an engagement portion of the mount, the engagement portion including:
      a first engagement member that includes a threaded inner surface of the ring that is arranged to threadedly engage a threaded portion of an outer surface of the inspection sensor; and
      a second engagement member that includes a cap arranged to receive therein an upper portion of the inspection sensor and a biasing member attached to the pair of attachment pads and arranged to bias the cap against the upper portion of the inspection sensor.

* * * * *